United States Patent [19]

Salmond

[11] 3,959,320

[45] May 25, 1976

[54] PROCESS AND COMPOUNDS

[75] Inventor: William G. Salmond, Kalamazoo, Mich.

[73] Assignee: The Upjohn Company, Kalamazoo, Mich.

[22] Filed: Sept. 23, 1974

[21] Appl. No.: 508,640

[52] U.S. Cl............................ 260/397.2; 260/397.5; 260/551 P
[51] Int. Cl.²........................................... C07J 9/00
[58] Field of Search...................... 260/397.2, 397.5

[56] References Cited
UNITED STATES PATENTS 3,822,254    7/1974    Patridge et al................ 260/239.55

*Primary Examiner*—Elbert L. Roberts
*Attorney, Agent, or Firm*—Martin B. Barancik; Roman Saliwanchik

[57] ABSTRACT

A method for preparing 25-hydroxycholesterol and novel intermediates.

19 Claims, No Drawings

PROCESS AND COMPOUNDS

BRIEF DESCRIPTION OF THE INVENTION

A new method for preparing 3α,5α-cyclo-6β-alkoxy-25-hydroxycholesterol has been discovered. This compound is an intermediate in the preparation of 25-hydroxycholecalciferol. This method comprises a. reacting 3α,5α-cyclo-6β-alkoxybisnorcholanaldehyde, alkoxy of one to six carbon atoms, inclusive, with (1) the phosphorane, $(C_6H_5)_3P=CBr_2$, or (2) the hexamethyl phosphorous triamide derivative $(Me_2N)_3P=CCl_2$ to form the 3α,5α-cyclo-6β-alkoxy-20S-(2',2'-dihalovinyl)pregnane.

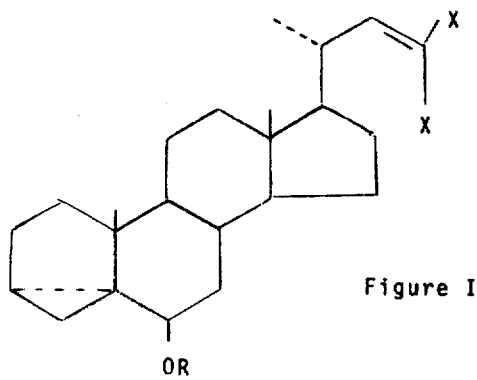

Figure I wherein R is alkyl of one to six carbon atoms, inclusive, and X is bromo or chloro;

b. reacting the dihalovinyl pregnane of FIG. I with an organolithium compound in an inert organic solvent at a reduced temperature, thereby forming the acetylene anion

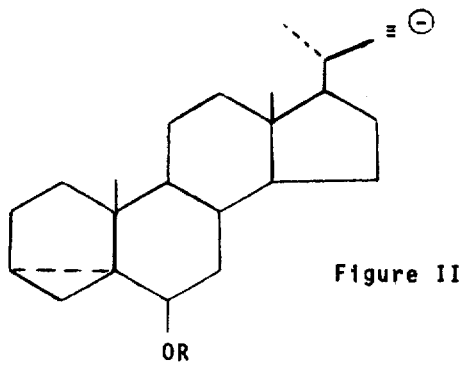

Figure II wherein R is as defined above;

c. reacting the acetylene anion of FIG. II with 2-methyl-propan-1,2-oxide at an elevated temperature and in an inert organic solvent to form the acetylenic alcohol

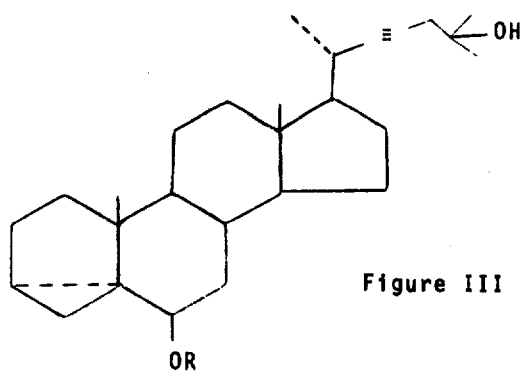

Figure III wherein R is as above defined;

d. catalytically hydrogenating the acetylenic alcohol of FIG. III to 3α,5α-cyclo-6β-alkoxy-25-hydroxycholesterol

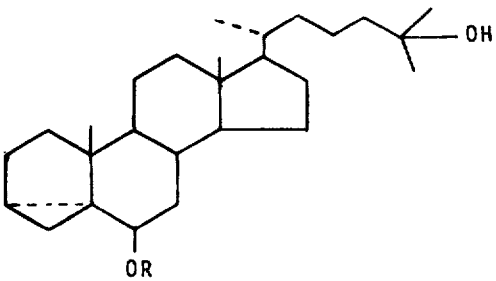

wherein R is as above defined.

Another aspect of the invention is the preparation of the dichlorovinyl pregnane of FIG. I by reacting the bisnorcholanaldehyde with the hexamethylphosphorous triamide derivative, $(Me_2N)_3P=CCl_2$.

A further aspect of the invention is reacting the dihalovinyl pregnane with an organolithium compound in an inert organic solvent at a temperature below −40°C., and thereafter reacting the acetylene anion of FIG. II with 2-methyl-propan-1,2-oxide at an elevated temperature and in an organic solvent to form the acetylenic alcohol of FIG. III.

A still further aspect of the invention is the reaction of the acetylene anion of FIG. II with 2-methyl-propan-1,2-oxide at an elevated temperature and in an organic solvent to form the acetylenic alcohol of FIG. III.

Another aspect of the invention is the preparation of $(Me_2N)_3P=CCl_2$ by the reaction of hexamethylphosphorous triamide with bromotrichloromethane.

A further aspect of the invention is the product formed from the reaction of hexamethylphosphorous triamide with bromotrichloromethane.

The following compounds are also part of the invention; $(Me_2N)_3P=CCl_2$ and compounds of the formula:

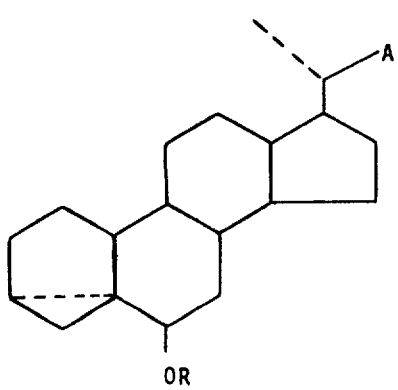

wherein R is alkyl of one to six carbon atoms, inclusive and A is selected from the group consisting of $-C\equiv C^\ominus$, $-C\equiv CH$, $-C\equiv C-CH_2C(CH_3)_2OH$, $(CH_2)_3C(CH_3)_2OH$, and

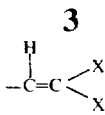

wherein X is bromo or chloro.

DETAILED DESCRIPTION OF THE INVENTION

The reagents which react with bisnorcholanaldehyde are prepared in the following manner: The phosphorane $(C_6H_5)_3P=CBr_2$, see F. Ramirez et al., *J.A.C.S.*, 84, 1745 (1962) and E. J. Corey and P. L. Fuchs, *Tet. Letters*, (1972), 3769 is synthesized by the reaction of triphenylphosphine with carbon tetrabromide.

The compound denominated as $(Me_2N)_3P=CCl_2$ is prepared from hexamethylphosphorous triamide, $(Me_2N)_3P$, and bromotrichloromethane. Although not positive of the structure of the compound, the reaction with a bisnorcholanaldehyde provides the vinyl chloride analogous to the reaction product of the same steroid with the brominated phosphorane. Consequently, an analogous structure for the ylide is a reasonable conclusion.

The reaction of the hexamethylphosphorous triamide with the bromotrichloromethane generally should have a molar excess of the amide to the halogenated methane of about 2. A molar excess in the range of from about 2 to about 3 is adequate. Since the reaction is quite vigorous, it is convenient to maintain the reaction vessel at a relatively low temperature, that is from about −30° to about 0°C., preferably from about −20° to about −10°C. Additionally, an inert organic solvent is advantageously employed as a heat sink for the reaction. Organic solvents such as halogenated alkanes, from one to four carbon atoms, inclusive, and ethers from four to about eight carbon atoms, inclusive, can be employed with facility. Illustrative examples of such solvents include methylene chloride, tetrachloroethane, tetrahydrofuran and diethyl ether.

The dihalovinylpregnane of FIG. I is prepared by addition of a bisnorcholanaldehyde to the haloalkylating agent prepared above. For convenient reaction methodology, the haloalkylating agent should be freshly prepared. The same organic solvent used in preparation of the haloalkylating agent may be used in this reaction as well, assuming a reasonable solubility of the bisnorcholanaldehyde therein. The temperature at which the reaction is carried out is not unduly significant. Temperature from about −20° to about +30°C., preferred from about −10° to about +10°C., can be employed.

The acetylenic anion of FIG. II is readily prepared from the reaction of the vinylpregnane of FIG. I with an organolithium reagent at reduced temperatures and in the presence of an inert organic solvent. Appropriate organolithium reagents are the lower alkyl reagents up through n-butyl, including isomers thereof and phenyl. A preferred organolithium reagent is n-butyllithium. The temperature at which the reaction is carried out should be kept below about −40°C. in order to lower the probability of undesirable side reactions. Preferred reaction temperature is below about −60°C. The minimum reaction temperature is dependent upon individual satisfaction with the reaction rate. Once the anion is produced, the temperature may be raised without significant deleterious effect. Any inert organic solvent can be employed. Examples of such solvents include ethers of four to eight carbon atoms, inclusive, alkanes of five to eight carbon atoms, inclusive, aryl of six to eight carbon atoms, inclusive. Illustrative examples include tetrahydrofuran, diethyl ether, hexane, benzene, pentane, 1,4-dioxane, heptane, and toluene.

The acetylenic anion of FIG. II may then be reacted directly with 2-methylpropan-1,2-oxide. Alternatively, the anion may be first "quenched", thereby forming the acetylene which may be stored at this point before reconverting into its anion and reacting with the epoxide. The acetylenic alcohol of FIG. III is formed using either procedure. Quenching occurs by contacting the acetylene anion with any reagent which is acidic relative to the anion of FIG. II, thereby resulting in the formation of the acetylene. Reagents which are satisfactory include water, methanol, or any suitable protic solvent.

The reaction of the anion with the epoxide is preferably carried out in the same solvent as that used in the preparation of the acetylene anion. Consequently, a similar scoping of solvents is intended here as with the preparation of the acetylene anion. The temperature of the reaction is not unduly significant. The higher the temperature, the faster the reaction rate. A temperature of from about 0°C. to the reflux temperature of the system can be employed. Higher temperature may be employed if pressure is applied to the reaction medium. For example, if the reaction of the acetylenic anion and the epoxide is carried out at room temperature in tetrahydrofuran, a prolonged time span of up to or greater than two days is required. The reaction time can be substantially lessened by the addition of hexamethylphosphoric triamide to the reaction vessel. The quantities added should be such that a substantial shortening of reaction time is achieved. Quantities of the triamide from about 1% up to about 10% of the reaction volume are effective. When the triamide is employed and the temperature of the reaction increased, advantageous reaction times are achieved. For example, when heated to about 60°C., the reaction takes place in about 3 hours.

The acetylenic alcohol of FIG. III is now catalytically hydrogenated to the 25-hydroxycholesterol of FIG. IV. This catalytic hydrogenation is carried out by convenient art known methods. For example, the acetylenic alcohol is hydrogenated with a noble metal catalyst in a suitable inert organic solvent at appropriate pressures. Platinum is a preferred noble metal. Inert organic solvents such as ethyl acetate, methylene chloride, and tetrahydrofuran can be employed. Ethyl acetate is preferred. Any hydrogenation pressure which brings about a reasonable rate of reaction can be employed. Pressures as low as 15 psi can be employed. The upper limit of pressure is dependent upon the loss of yield from the opening of the cyclopropane ring. Pressure up to about 100 psi or even higher can be employed with facility.

Following are examples illustrative of the inventive scope. They are meant to exemplify and not to restrict the invention. All $R_f$'s refer to a silica gel system.

EXAMPLE 1

3α,5α-cyclo-6β-Methoxy-20S-(2',2'-dibromovinyl)-pregnane

Carbon tetrabromide (12.0 g.) is added to a solution of triphenylphosphine (18.9 g.) in 150 ml. methylene chloride at −6°. After 20 minutes a solution of 3α,5α-cyclo-6β-methoxybisnorcholanaldehyde (6.2 g.) in methylene chloride (50 ml.) is added during 20 minutes while maintaining the temperature between −6° and −3°C. The reaction solution is concentrated at 0°C. to ca. 150 ml. Skellysolve B (50 ml.) is added to yield a white precipitate. This is filtered off and the reaction mixture is again concentrated to ca. 150 ml. at 0° and again Skellysolve B (50 ml.) is added. The precipitated solid is again filtered off and this procedure is repeated four times. Then the mixture is stirred at 0°C. for 1 hour before filtering. The filtrate is evaporated to give an oil which is dissolved in 50 ml. acetone. After a period of ca. 16 hours at 0°C. the crystalline product is removed by filtration to give the desired material, m.p. 85°–89°.

NMR (CDCl$_3$): δ 0.30–0.63; 0.77s (3H); 1.03s (3H); 1.03d J=7Hz (3H); 2.77bt J=ca. 2Hz (1H); 3.32s (3H); 6.18d J=10Hz (1H).

R$_f$: 10% ethyl acetate/Skellysolve B — 0.66.

EXAMPLE 2

3α,5α-cyclo-6β-Methoxy-20S-ethynylpregnane

A solution of n-butyllithium (32 ml. of a 1.5M solution in hexane) is added to a solution of the dibromovinylpregnane compound of Example 1 in 100 ml. dry tetrahydrofuran at −70°C. After 30 minutes the temperature is allowed to rise to ca. 20° and left there for a further 30 minutes. The solution is quenched with water and then the whole mixture poured into water and extracted with Skellysolve B, a mixture of isomeric hexanes. The extracts are washed with water, dried and evaporated to give an oil which is crystallized from ethanol to give the acetylene, m.p. 74°–76°.

NMR (CDCl$_3$): δ 0.30–0.63; 0.75s (3H); 1.03s (3H); 1.23d J=7Hz (3H); 2.0 J=2.5Hz (1H); 2.78bt. J=ca. 2Hz (1H); 3.33s (3H);

R$_f$: 10% ethyl acetate/Skellysolve B — 0.25.

EXAMPLE 3

3α,5α-cyclo-6β-Methoxy-25-hydroxy-cholest-22-yne

To a solution of the acetylene of Example 2 (1.7 g.) in 25 ml. dry tetrahydrofuran and 2.5 ml. hexamethylphosphoric triamide is added n-butyllithium (4.0 ml. of a 1.4M solution in hexane) at room temperature. 2-methylpropan-1,2-oxide (2 ml.) is added and the mixture left at room temperature for 2 days. After quenching with water, the mixture is extracted with ethyl acetate. The extracts are washed with water, dried and evaporated to yield the alcohol as an oil.

NMR (CDCl$_3$): δ 0.30–0.63; 0.77s (3H); 1.03s (3H); 1.20d J=7Hz (3H); 1.27s (6H); 2.33bd J=ca. 2Hz (2H); 2.78bt J=ca. 2Hz (1H); 3.33s (3H).

R$_f$: 10% ethyl acetate/Skellysolve B — 0.60.

EXAMPLE 4

Conversion of 3α,5α-cyclo-6β-methoxy-20S-(2',2'-dibromovinyl)-pregnane directly into 3α,5α-cyclo-6β-methoxy-25-hydroxycholest-22-yne To a solution of the dibromovinylpregnane of Example 1, (0.5 g.) in 2 ml. dry tetrahydrofuran at −25°C., 1.6 ml. of n-butyllithium in hexane (1.6 M) is added. After 15 minutes at this temperature 0.2 ml. hexamethylphosphoric triamide and 1 ml. 2-methylpropan-1,2-oxide are added. The reaction vessel is sealed and heated to 60°C. After 3 hours, the reaction mixture is poured into water and extracted with ethyl acetate. The extracts are washed, dried and evaporated to yield an oil of the alcohol.

EXAMPLE 5

3α,5α-cyclo-6β-methoxy-20S-(2',2'-dichlorovinyl)-pregnane

To a solution of bromotrichloromethane (1.98 g.) in dry methylene chloride (20 ml.) at −10°C. is added during 30 minutes a solution of hexamethylphosphoric triamide (3.26 g.) in dry methylene chloride (30 ml.) to give a dark brown solution. The temperature is kept below −5°C. during this addition. 3α,5α-cyclo-6β-methoxybisnorcholanaldehyde (1.0 g.) in 10 ml. dry methylene chloride is added all at once. After 10 minutes the reaction mixture is poured into water and extracted with Skellysolve B. The virtually colorless extracts are washed with water, dried and evaporated to give the dichlorovinylpregnane as an oil.

NMR (CDCl$_3$): δ 0.30–0.63; 0.77s (3H); 1.03s (3H); 1.03d J=7 (3H); 2.77bt J=ca. 2 (1H); 3.32s (3H); 5.67d J=10 (1H).

R$_f$: 10% ethyl cetate/Skellysolve B — 0.65.

EXAMPLE 6

3α,5α-cyclo-6β-Methoxy-20S-ethynylpregnane

To a solution of the crude dichloro compound of Example 5 (200 mgs.) in 4 ml. dry tetrahydrofuran at −70°C. is added 1.0 ml. of n-butyllithium solution in hexane (1.6 M). After 5 minutes the temperature is allowed to rise to ca. 20°C. and after 15 minutes at this temperature, the reaction mixture is quenched with water and extracted with Skellysolve B. The extracts are washed with water, dried and evaporated to yield an oil which is crystallized from ethanol to give the acetylene identical with that obtained in Example 2.

EXAMPLE 7

3α,5α-cyclo-6β-Methoxy-25-hydroxycholesterol

The acetylenic alcohol 3α,5α-cyclo-6β-methoxy 25-hydroxycholest-22-yne (800 mgs.) in 10 ml. ethyl acetate is added to a suspension of a platinum catalyst in 20 ml. ethyl acetate (prepared by reduction of 1.0 g. platinum oxide for 30 minutes at 15 psi). The mixture is hydrogenated at 45 psi for 1.5 hours. The solution is then filtered from the catalyst and evaporated to yield a crystalline residue. This residue is recrystallized from acetonitrile to give the hydroxy cholesterol, m.p. 144°–146°.

I claim:

1. A method for preparing 3α,5α-cyclo-6β-alkoxy 25-hydroxycholesterol wherein alkoxy is from one to six carbon atoms, inclusive, which comprises a. reacting 3α,5α-cyclo-6β-alkoxybisnorcholanaldehyde, alkoxy of one to six carbon atoms, inclusive, with
   1. the phosphorane, $(C_6H_5)_3P=CBr_2$ or
   2. the hexamethylphosphorous triamide derivative $(Me_2N)_3P=CCl_2$ to form the 3α,5α-cyclo-6β-alkoxy-20S-(2',2'-dihalovinyl)pregnane

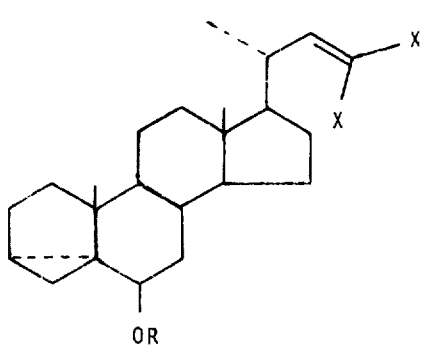

wherein R is alkyl of one to six carbon atoms, inclusive, and X is bromo or chloro;

b. reacting the said dihalovinyl pregnane with an organolithium compound wherein organo is selected from the group consisting of alkyl of one to four carbon atoms, inclusive, and phenyl in an inert organic solvent at a reduced temperature to produce the acetylene anion

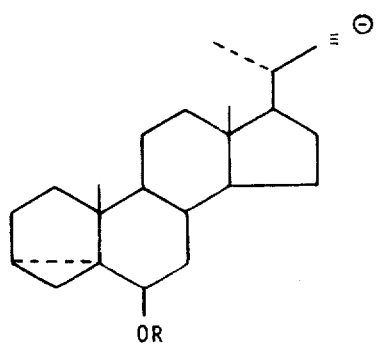

wherein R is as defined above c. reacting the said acetylene anion with 2-methylpropan-1,2-oxide at an elevated temperature and in an inert organic solvent to form the acetylenic alcohol

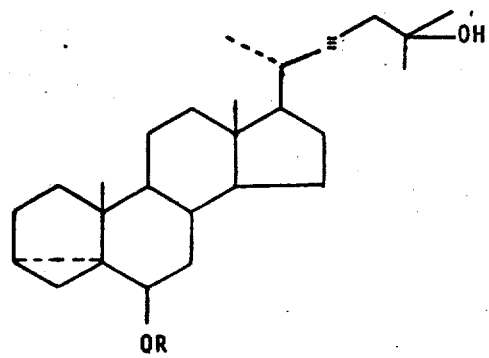

wherein R is as above defined d. saturating the triple bond of the said acetylenic alcohol to form 3α,5α-cyclo-6β-alkoxy-25-hydroxycholesterol

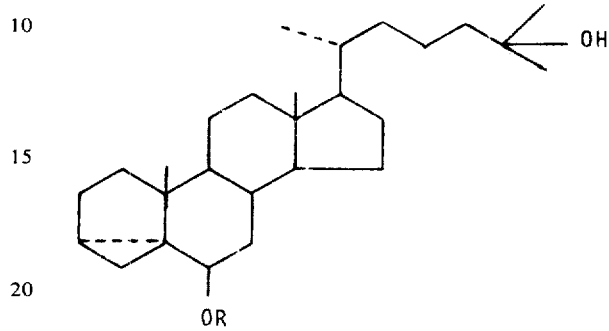

wherein R is alkyl of one to six carbon atoms, inclusive.

2. A method in accordance with claim 1 wherein the acetylene anion of Step b is prepared at a temperature below about −40°C.

3. A method in accordance with claim 2 wherein the temperature is below about −60°C.

4. A method in accordance with claim 1 wherein hexamethylphosphoric triamide is present in sufficient quantities to accelerate the reaction of the conversion of the acetylene anion to the acetylenic alcohol.

5. A method in accordance with claim 4 wherein the acetylene anion of Step b is prepared at a temperature below about −40°C.

6. A method in accordance with claim 1 wherein the acetylene anion is quenched to the acetylene.

7. A method in accordance with claim 2 wherein the organolithium reagent is n-butyllithium.

8. A method in accordance with claim 5 wherein the organolithium reagent is n-butyllithium.

9. A method for preparing 3α,5α-cyclo-6β-alkoxy-20S-(2',2'-dichlorovinyl)pregnane, wherein alkoxy is from one to six carbon atoms which comprises reacting a compound of the formula

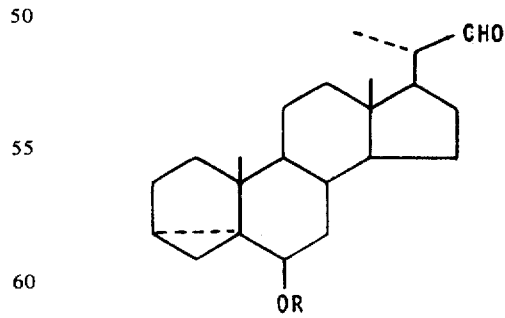

wherein R is from one to six carbon atoms, inclusive, with the hexamethylphosphorous triamide derivative, $(Me_2N)_3P=CCl_2$.

10. A method for preparing compounds of the formula

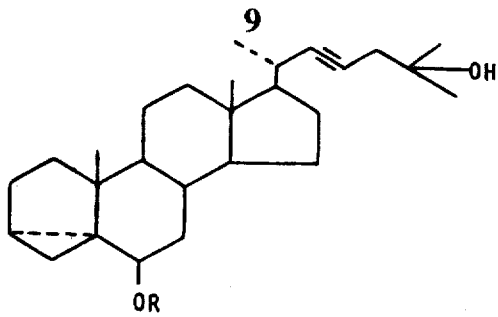

wherein R is one to six carbon atoms, inclusive, which comprises reacting

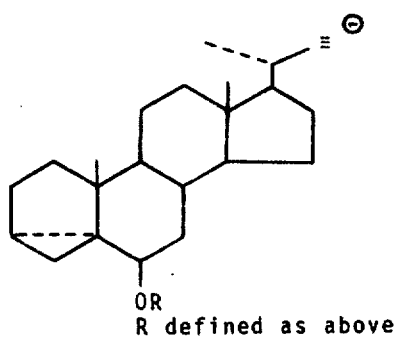

R defined as above with 2-methyl-propan-1,2-oxide in an organic solvent.

11. A method in accordance with claim 10 wherein hexamethylphosphoric triamide is present in the reaction vessel in quantities sufficient to accelerate the reaction time.

12. A method in accordance with claim 10 wherein the acetylenic anion is prepared by reacting 3α,5α-cyclo-6β-alkoxy-20S-(2′,2′-dihalovinyl)pregnane wherein alkoxy is one to six carbon atoms, inclusive, and the halo substituents are both bromine or both chlorine with an organolithium reagent wherein organo is selected from the group consisting of alkyl of one to four carbon atoms, inclusive, and phenyl in an inert organic solvent at a temperature below −40°C.

13. A method in accordance with claim 12 wherein hexamethylphosphoric triamide is present in the reaction vessel in quantities sufficient to accelerate the reaction time of forming the said acetylenic alcohol.

14. A method in accordance with claim 13 wherein n-butyllithium is the organolithium reagent.

15. Compounds of the formula

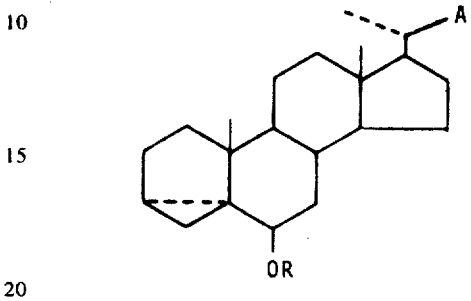

wherein R is alkyl of one to six carbon atms, inclusive, and A is selected from the group consisting of —C≡C—H, —C≡C⊖, —C≡C—CH$_2$—C(CH$_3$)$_2$OH,

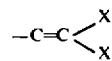

wherein X is chloro or bromo.

16. Compounds in accordance with claim 15 wherein A is —C≡C—H or —C≡C⊖.

17. Compounds in accordance with claim 15 wherein A is

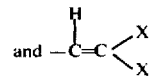

wherein X is chloro or bromo.

18. A compound in accordance with claim 15 wherein A is C≡C—CH$_2$—C(CH$_3$)$_2$OH.

19. Compounds in accordance with claim 15 wherein R is alkyl of one to three carbon atoms, inclusive.

* * * * *